United States Patent [19]
Collins

[11] Patent Number: 5,649,944
[45] Date of Patent: Jul. 22, 1997

[54] APPARATUS FOR PREPARING CORNEA MATERIAL FOR TABBED (SUTURELESS) TRANSPLANTATION

[76] Inventor: Joseph Patrick Collins, 7517 Fourth Ave. North, St. Petersburg, Fla. 33710

[21] Appl. No.: 329,709

[22] Filed: Oct. 26, 1994

Related U.S. Application Data

[63] Continuation-in-part of Ser. No. 289,670, Aug. 12, 1994, Pat. No. 5,584,881.

[51] Int. Cl.⁶ .................................................. A61B 17/32
[52] U.S. Cl. .................................................. 606/166
[58] Field of Search ........................ 606/166, 184, 606/179; 128/753, 754

[56] References Cited

U.S. PATENT DOCUMENTS

| | | | |
|---|---|---|---|
| 3,454,966 | 7/1969 | Rosen | 3/13 |
| 3,945,054 | 3/1976 | Fedorov et al. | 3/13 |
| 4,077,411 | 3/1978 | Ward | 606/166 |
| 4,127,903 | 12/1978 | Schachar | 3/13 |
| 4,190,050 | 2/1980 | Bailey | 128/305.1 |
| 4,236,519 | 12/1980 | La Russa et al. | 128/305 |
| 4,429,696 | 2/1984 | Hanna | 128/310 |
| 4,563,779 | 1/1986 | Kelman | 623/5 |
| 4,612,012 | 9/1986 | White | 623/5 |
| 4,662,881 | 5/1987 | Nordan | 623/5 |
| 4,718,420 | 1/1988 | Lemp | 128/310 |
| 4,772,283 | 9/1988 | White | 623/5 |
| 4,807,623 | 2/1989 | Lieberman | 128/305 |
| 4,810,082 | 3/1989 | Abel, Jr. | 351/160 R |
| 4,824,066 | 4/1989 | Smith | 248/500 |
| 4,834,748 | 5/1989 | McDonald | 623/5 |
| 4,842,599 | 6/1989 | Bronstein | 623/5 |
| 4,865,033 | 9/1989 | Krumeich et al. | 606/166 |
| 4,884,570 | 12/1989 | Krumeich et al. | 606/166 |
| 5,011,498 | 4/1991 | Krumeich et al. | 606/166 |
| 5,030,230 | 7/1991 | White | 623/5 |
| 5,139,518 | 8/1992 | White | 623/5 |
| 5,290,301 | 3/1994 | Lieberman | 606/166 |
| 5,464,417 | 11/1995 | Elick | 606/166 |

FOREIGN PATENT DOCUMENTS

| | | | |
|---|---|---|---|
| 1657180 | 6/1991 | U.S.S.R. | 606/166 |
| WO93/08878 | 5/1993 | WIPO . | |

*Primary Examiner*—Michael H. Thaler
*Attorney, Agent, or Firm*—Foley & Lardner

[57] ABSTRACT

A tool and a method for preparing a donor material used in sutureless corneal transplants uses a first cutting portion to prepare a donor blank having tabbed portions extending outwardly radially. A second cutting portion is used to cut the central portion of the blank. The tool is used as a guide member for the second cutting portion. In one embodiment the tool has slits laterally defined therethrough which allow the tabbed portions of the donor material to be thinned to a desired thickness using a scalpel. In an another embodiment the second cutting portion is a round trephine which is used to simultaneously trim each of the tabbed portions.

2 Claims, 12 Drawing Sheets

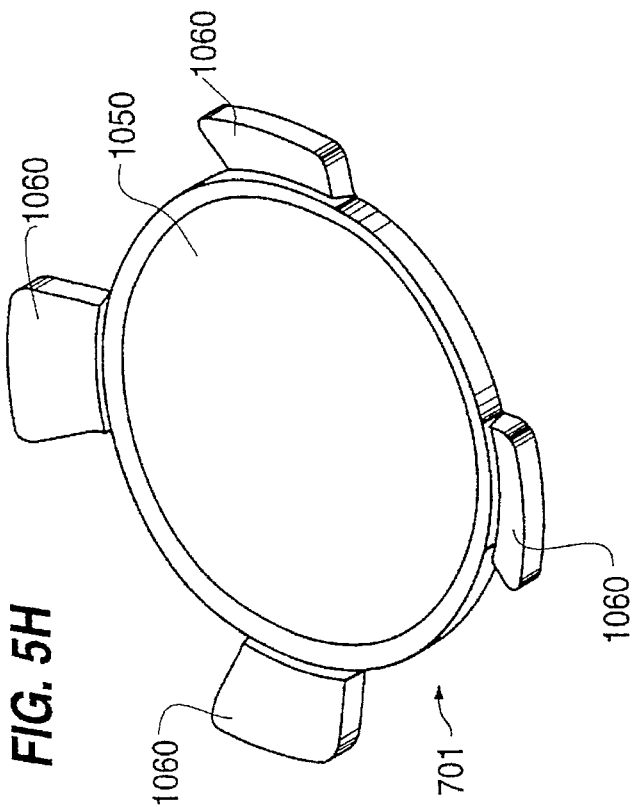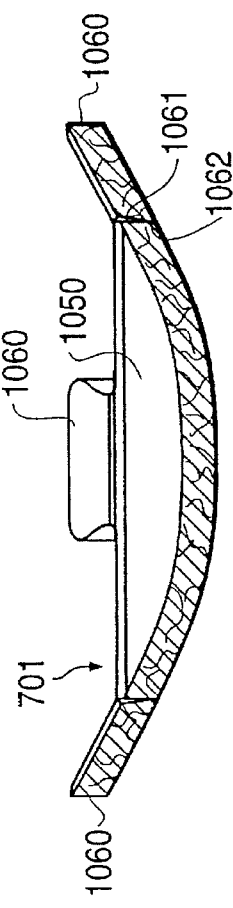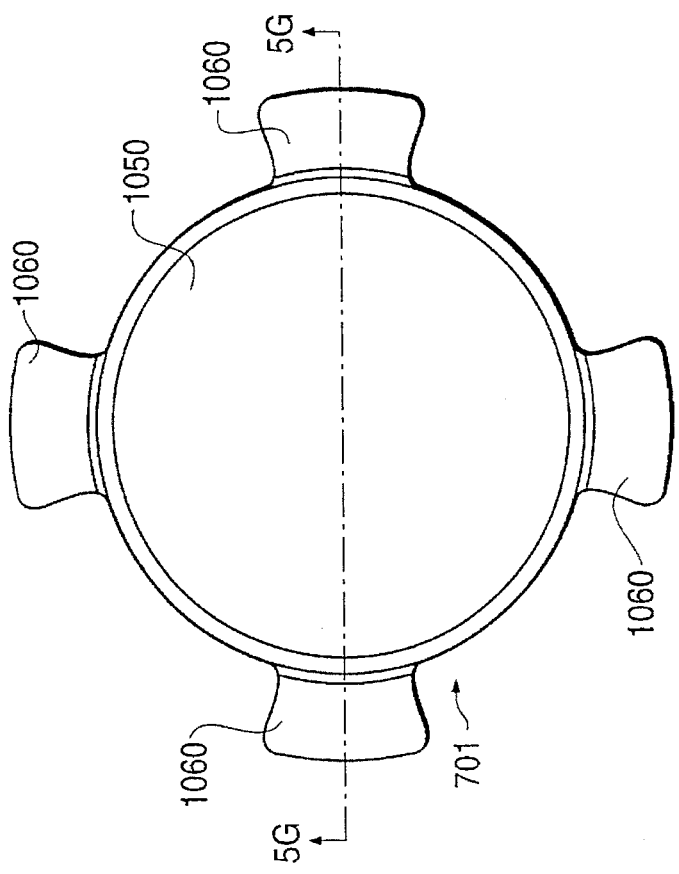

APPARATUS FOR PREPARING CORNEA MATERIAL FOR TABBED (SUTURELESS) TRANSPLANTATION

This application is a Continuation-In-Part (CIP) of U.S. patent application Ser. No. 08/289,670, filed Aug. 12, 1994, now Pat. No. 5,584,881 the contents of which are herein incorporated by reference.

The United States Government has rights in this invention pursuant to contract no. DE-AC04-92AL73000 between the United States Department of Energy and Martin Marietta Specialty Components, Inc.

BACKGROUND OF THE INVENTION

This invention relates to the preparation of donor material for a sutureless corneal transplantation, and more particularly, to a method and apparatus for precisely cutting and preparing the donor material including tabs used for transplanting corneas without the use of sutures.

Corneal transplantation occurs in approximately 37,000 patients in the United States each year. In most conventional transplantations, healing of the recipient's eye is delayed because of the avascular nature of the corneal. The stromal wound healing is facilitated by sutures. However, sutures used in many conventional corneal transplants induce astigmatism. More recently, a sutureless method for corneal transplantation has been developed by Dr. James Rowsey (Rowsey corneal transplant).

FIG. 1 illustrates the Rowsey corneal transplant using the tabbed (sutureless) method. In FIG. 1, a donor material 102 is formed in the shape of a partial sphere having a center portion 103 the size and shape of a central portion of the cornea of an eye. The center portion 103 has a periphery including a downward extending portion 110 and an exterior surface 105 in a convex configuration and an interior surface 107 in a concave configuration with an essentially common thickness throughout. The donor material 102 includes a plurality of corneal tabs 106 extending radially from the periphery of the center portion 103. The top (exterior) surfaces of the tabs 106 are a continuation of the exterior surface 105 of the center portion 103. The exterior surfaces of the center portion 103 (bordered by dotted lines in FIG. 1) and the tabs 106 are of a common Bowman's membrane 108a typically having a thickness of about 100 microns. These tabs typically have a thickness of about 10 percent of the thickness of the center portion 103 of the donor material.

Also illustrated in FIG. 1 is the recipient eye 104. The eye 104 is in the shape of a partial sphere. The recipient eye 104 is formed with a circular aperture 112 at its central portion. The circular aperture 112 is of a size and shape corresponding essentially to the periphery of the center portion 103 and extending portion 110 of the donor material 102. The periphery of the aperture 112 is of a common thickness. The recipient eye 104 also includes a plurality of symmetrically positioned pockets 114. The pockets 114 are incisions made into the thickness of the cornea preferably just under the Bowman's membrane 108b of the recipient eye 104 into the periphery of the aperture 112.

To carry out the transplantation, the central portion 103 of the donor material 102 is positioned within the aperture 112 of the recipient eye 104. The tabbed portions 106 are imbricated into the pockets 114 of the recipient eye 104. Forceps are preferably used for positioning the central portion 103 into the recipient eye 104 and the tabs 106 into their respective pockets 114. Although temporary sutures may also be used to pull the tabs 106 into the pockets 114, in no instance is it necessary to suture the recipient's visual field as is required in conventional transplantation techniques.

Using the above described method, the donor material 102 can be implanted into the recipient eye 104 without the use of sutures in the center portion 103 of the donor material 102. FIG. 2 illustrates a repaired eye with the transplanted cornea. Like reference numerals are used in FIG. 2 to correspond to those elements illustrated in FIG. 1. As can be seen in FIG. 2, the tabbed portions 106 lie within the pockets 114 of the recipient eye 104 and are covered by the Bowman's membrane 108b of the recipient eye 104. The center portion 103 including the downward extending portion 110 of the donor material 102 is placed within the aperture 112 of the recipient eye 104. In this manner, a cornea transplant is carried out in a more simple and straightforward manner without the need for sutures. This method is more fully described in the above-named prior application to which benefit of a filing date is relied upon.

Heretofore, a satisfactory method for preparing the donor material 102 with the necessary precision has not been developed. It is extremely difficult and time consuming to manually prepare a tabbed donor cornea 102 as illustrated in FIG. 1. Moreover, the circle to circle fit from the donor to recipient may leave gaps and/or bulges when manual preparation is used. The radial placement of the donor tabs would be haphazard at best and each implanted cornea would need to be used as the transfer template to prepare the recipient eye. This causes the length of time from the donor to recipient to increase correspondingly and thereby increase the likelihood of damage to the donor material.

Previous efforts to design a tool to carry out the preparation of the donor material 102 have been based on elaborate schemes using plural circular cutting blades combined with linear radial extending blades in order to prepare the tabbed material having the round center portion and the tabbed radially extended portions. Such conventionally suggested tools, however, are unworkable in that the precision required to fashion such a tool is not practical or possible and have not been seriously pursued. Moreover, an extremely important aspect of the sutureless corneal transplant is the ability to prepare the tabbed portions sufficiently thin for insertion into the pockets of the recipient eye. Conventionally suggested designs have not been adequate to accomplish this goal.

A further difficulty encountered by conventional techniques for preparing the donor material, arises from the nature of the donor material to be cut. The donor material exhibits properties very much like innertube tire rubber. The properties of the material make it extremely difficult to cut through the donor material with the precision necessary to prepare the tabbed donor form. Accordingly, a tool used to cut the donor material should also be designed to support the donor material as it is being cut.

It is, therefore, an object of the instant invention to provide a tool which can be used to create replacement cornea including multiple tabs from a donor cornea in a straight forward manner and which is sufficiently precise to properly prepare that the donor material.

BRIEF DESCRIPTION OF THE DRAWINGS

A more complete understanding of the nature and objects of the instant invention can be had by reference to the following detailed description taken in connection with the accompanying drawings in which:

FIGS. 5A–5K illustrate sequentially the appearance of the donor material during the corneal preparation according to a method of the instant invention;

DETAILED DESCRIPTION OF THE PREFERRED EMBODIMENTS

Figure 3A:
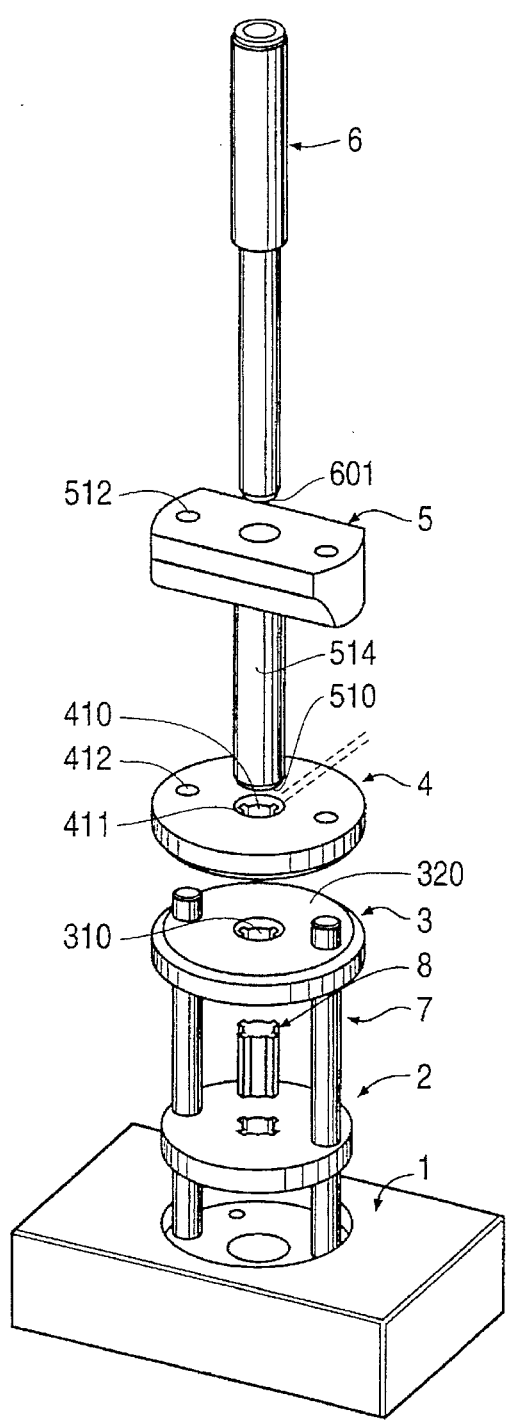
FIGS. 3A–3D illustrate a tool for carrying out the preparation of the donor material according to an embodiment of the instant invention.
Figure 3B:
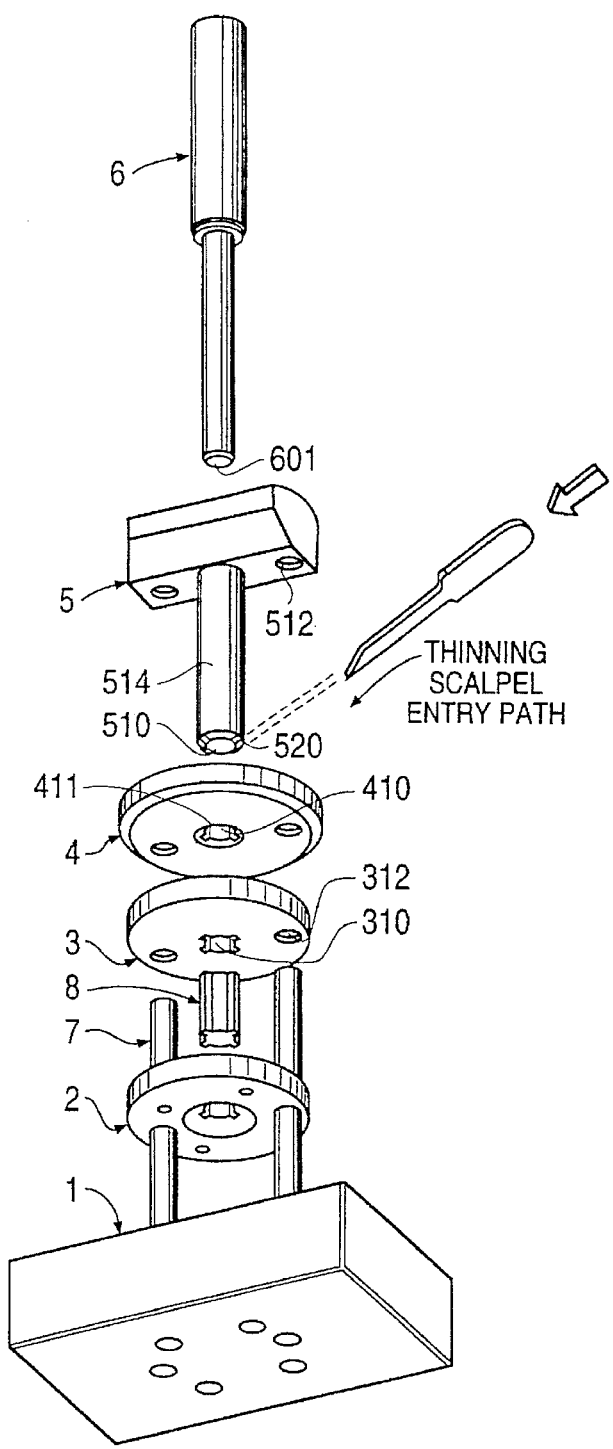

FIGS. 3A–3D illustrate an apparatus (or tool) used for preparation of the donor material 102 (FIG. 1) according to an embodiment of the instant invention. As illustrated in FIGS. 3A and 3B, a base 1 is provided to support the tool. Guide pins 7 extending up from the base 1 support a punch base 2. A punch 8 is held in place within the punch base 2. The punch 8 (shown in greater detail in FIG. 3D) has a shape corresponding to that of the top surface of the donor material to be prepared. That is, the surface on the top end of the punch has a concave spherical radius at its center portion 806 and tabbed portions 802 extending radially from a central axis of the system and the punch corresponding to the tabbed portions 106 (FIG. 1) of the donor material. A nest 3 having a centrally located nest hole 310, also having a shape corresponding substantially to the desired shape of the donor material, is aligned along the central axis and is adapted to receive the punch 8 in the nest hole 310. The nest 3 has guide holes 312 located on the periphery of the nest in order to receive the guide pins 7. The nest hole 310 is such that the periphery of the punch 8 fits closely within the nest hole 310.

A die 4 is aligned along the central axis to be positioned above the nest 3 and guided by guide pins 7. The die also has a hole 410 centrally located which corresponds to the shape of the donor material. The die 4 is provided to cut through the donor material to prepare a donor blank as more fully described below. The central portion 411 of the die 4 is illustrated in greater detail in FIG. 3C. Portions of an upper surface of the central portion 411 of the die 4 act as a lower scalpel guide 401. The operation of the scalpel guide will be more fully explained below. The die 4 is adapted to receive the punch 8 such that the extending tabbed portions 802 (FIG. 3D) of the punch 8 are received by the recessed portions 402 of the die 4. The die 4 also includes guide holes 412 (FIGS. 3A and 3B) which are adapted to receive the guide pins 7 for alignment. A bottom portion of die 4 which defines the periphery where it intersects the hole 410 acts as a cutting edge 422 in combination with a cutting edge 822 of the punch 8 which is defined by the intersection of the surfaces 802 and 806 and the vertical outside surface 824 of the punch 8. The peripheral clearance between the punch 8 and the die 4 at the recessed portions 402 cannot exceed 0.0001".

A hollow guide member 5 is adapted to be aligned by the guide pins 7 via guide holes 512. A downwardly extending cylindrical portion 514 of the hollow guide member 5 includes a bottom end 510 adapted to engage and rest on a portion of the top surface of the die 4. The hollow guide 5 also includes lateral slots 520 through a portion of the bottom end 510 which serve to form an upper scalpel guide. The lateral slots 520 in the guide member 5 are aligned with the lower scalpel guide 401 (FIG. 3C) of the die 4.

A round trephine 6 (FIGS. 3A and 3B) having a round cutting edge 601 on a bottom end thereof is received by the guide member 5. The guide member 5 serves to guide the round trephine 6 to the donor blank material resting on the punch 8 after the die 4 has been used to prepare the donor blank. The trephine 6 is used to make a circular cut into the donor blank as more fully described below. In other words, the cutting edge of the round trephine 6 extends through the guide member 5 and out the bottom end 510 of the guide member 5, which is in contact with the die 4, and cuts into the donor material.

The operation of the device illustrated in FIGS. 3A–3D will now be more fully described in connection with FIGS. 3A–3D, 4 and 5A–5K. Prior to use, all the instruments should be sterile. Moreover, the corneal tissue should not be exposed to any instrument parts which are not at room temperature. In operation, the nest 3 is placed on the guide pins 7 and lowered until its upper surface 320 is coincident with the periphery of the punch 8. This provides a place to rest the donor cornea material in preparation for the upcoming operation. The donor material 1020 (in the shape shown in FIG. 5A) is placed centrally on the nest 3 with the endothelium facing upward. The donor material 102 is secured in place by generating a vacuum beneath the material on the punch 108. The vacuum may be produced, for example, using a syringe (not shown) connected to produce a vacuum at the surface 806 (FIG. 3D) of the punch via holes 804. It is noted that during the process, the corneal endothelium cell layer should only be touched in those areas which are eventually removed and discarded.

Figure 4:
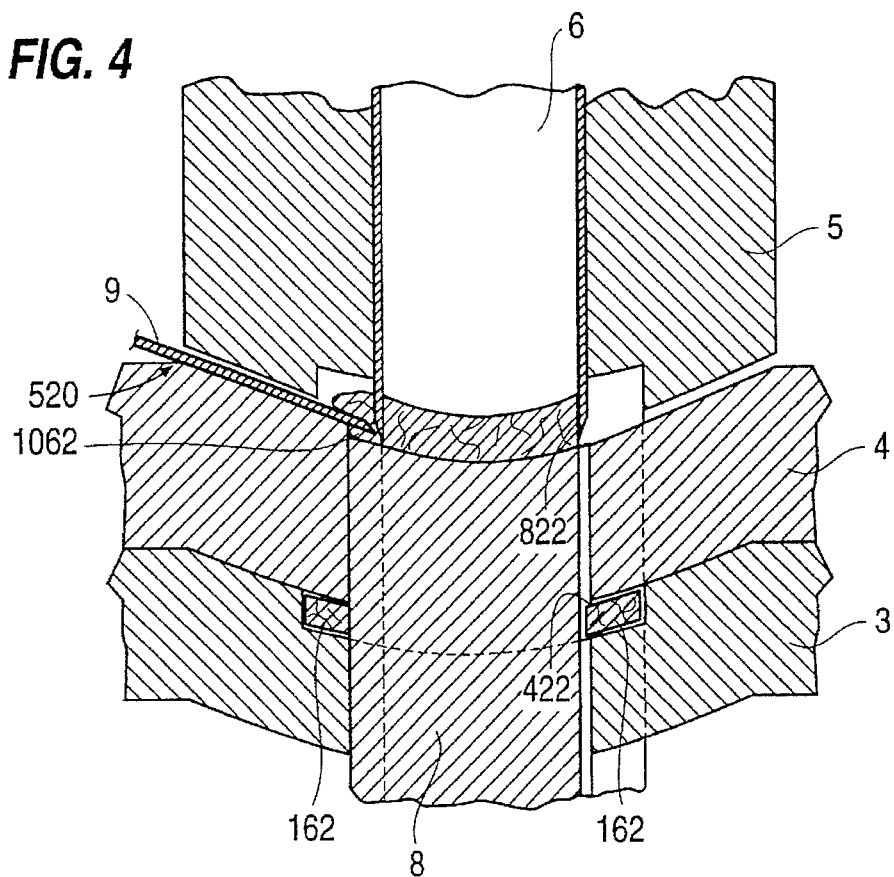
FIG. 4 illustrates the cooperation of the various elements depicted in FIGS. 3A–3D when the tool is being used.
Figure 5A:
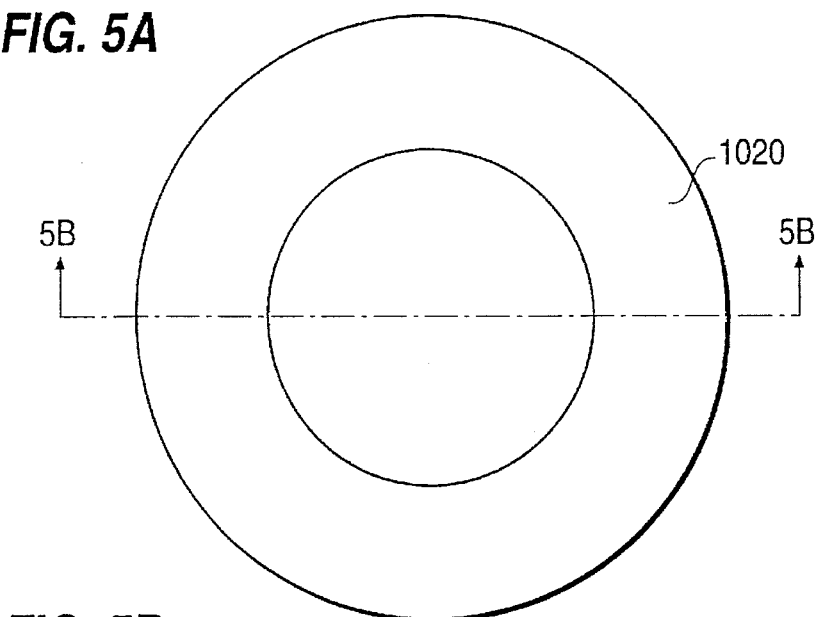
Figure 5B:
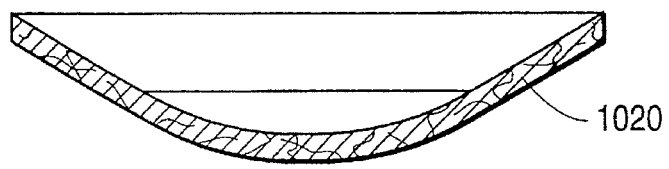
Figure 5E:
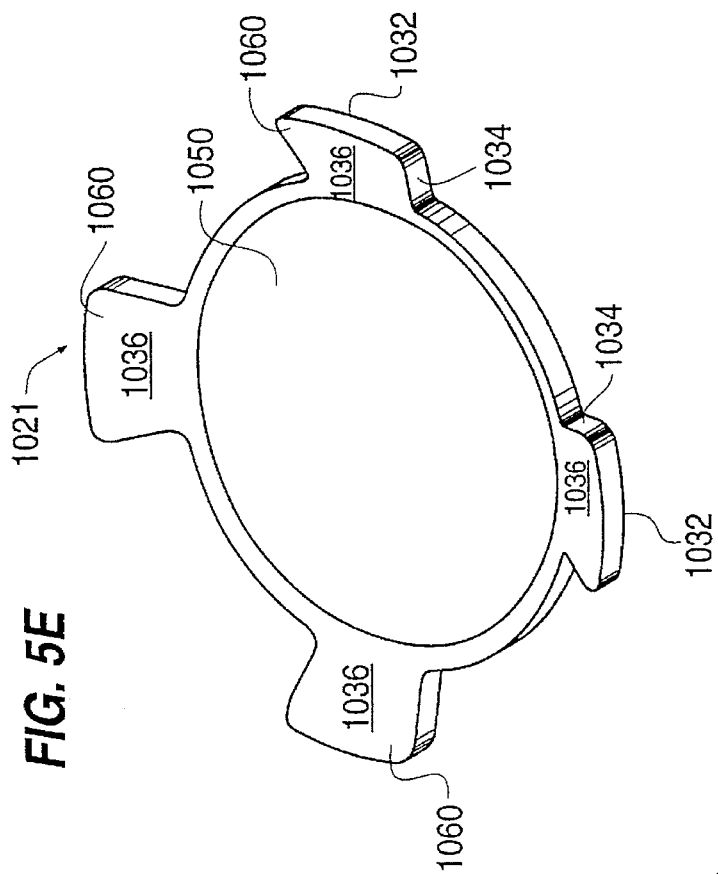
Figure 5C:
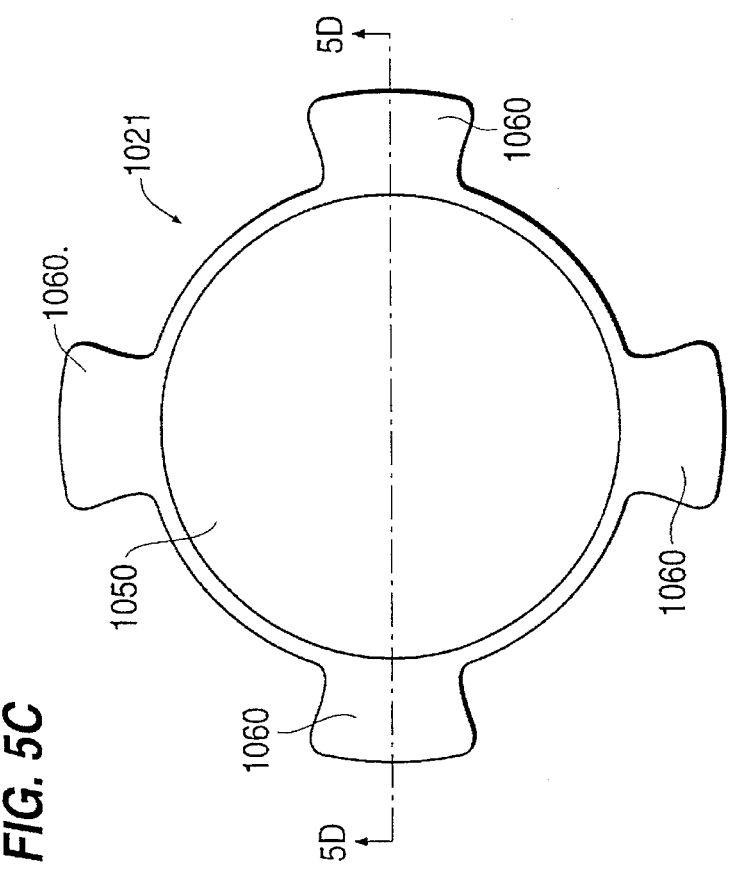
Figure 5D:
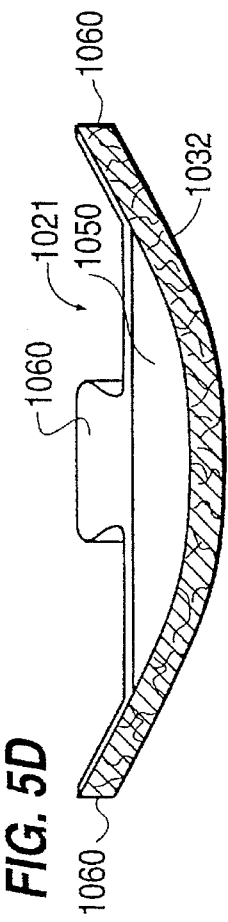

Once the donor material is in place on the nest 3, the die 4 is installed on the guide pins 7 and brought downward until the donor material 1020 is cut to produce a donor blank 1021 having the tabbed shape depicted in FIG. 5C. The scrap portion 162 (FIG. 4) goes down around punch 8 in the nest 3 and is discarded later. The die 4 descends until the surface of the lower scalpel guide 401 (FIG. 3C) is higher than the punch cutting edge 822 (FIG. 3D) by the thickness of the Bowman's membrane, 100 µm (0.004"). In the configuration illustrated in FIGS. 3A and 3B, the die should be gripped at the guide pins 7 in order to avoid cocking.

Once the tabbed blank 1021 (FIG. 5C) is produced and inspected to insure correct peripheral cutting, the hollow guide member 5 is assembled onto the guide pins 7 (FIGS. 3A and 3B). The hollow guide member 5 is lowered until it bottoms out (i.e., comes into contact with the top of die 4). At this point the tabbed blank 1021 is resting on the punch 8 with a portion of the tabbed blank 1021 extending upward above the top surface of lower scalpel guide 401 of the die 4. The guide 5 and the die 4 are shaped such that the tabs 1060 of the tabbed blank 1021 are now completely enclosed on 4 planes by the tool. Specifically, the lower surface 1032 (FIG. 5D) of the tabs 1060 is supported by the punch 8. The radially extending sides 1034 (FIG. 5E) of the tabs 1060 are surrounded by the die 4. The top portion 1036 of the tabs 1060 is enclosed by the guide member 5.

Figure 5K:
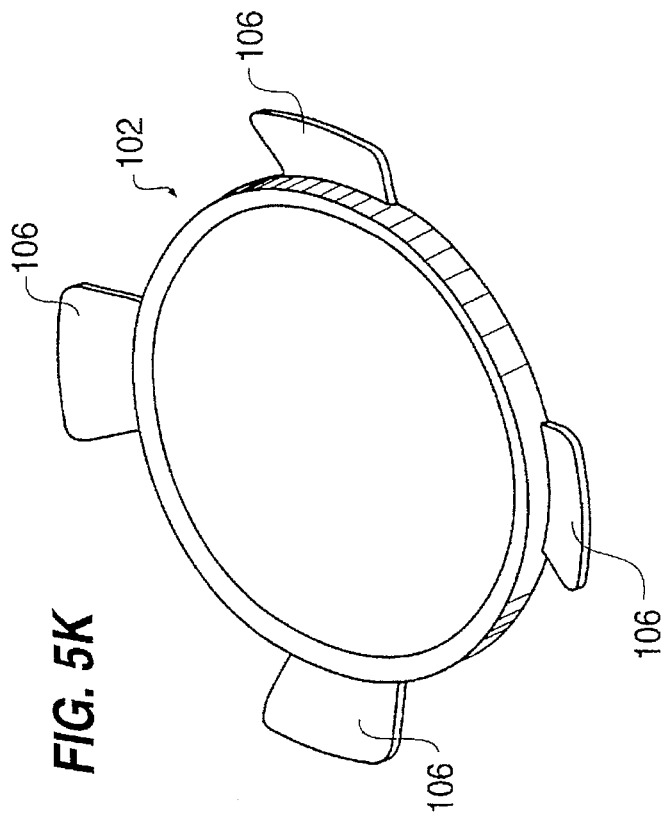
Figure 5I:
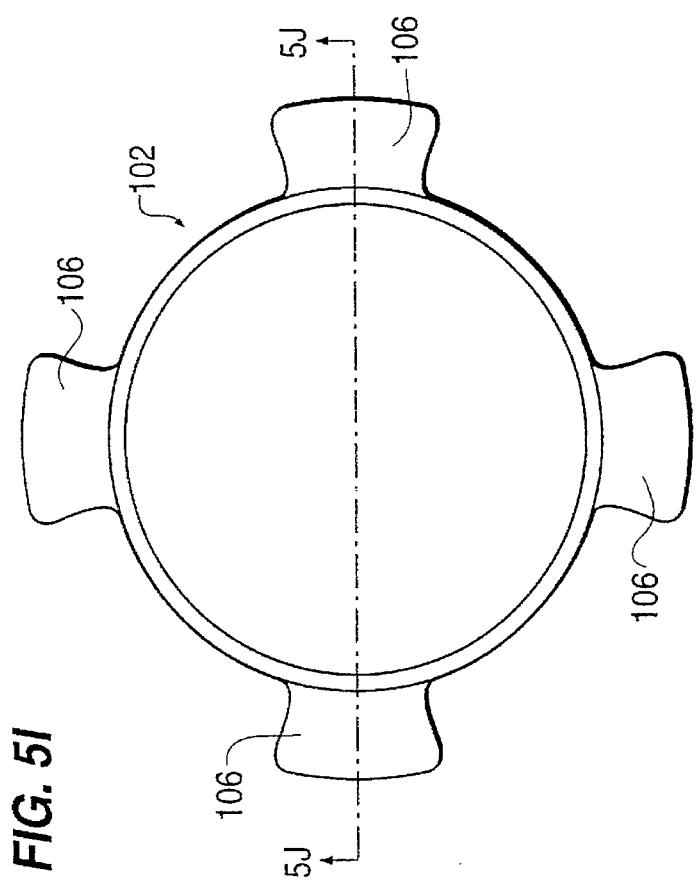
Figure 5J:
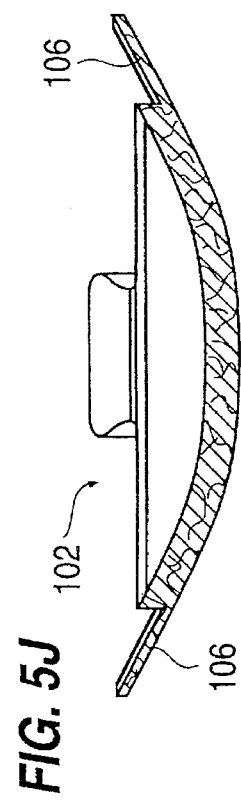

A round trephine 6 is inserted into the hollow guide member 5 FIGS. 3A and 3B. The round trephine 6 is lowered using an oscillating motion until it reaches its lowest point just above the Bowman's membrane, 1062 (FIGS. 4 and 5G). At its lowest point, the trephine 6 cuts into the stroma between the tabs 106 and the central portion 103 of the donor tabbed blank 1021 down to the Bowman's membrane 1062. Specifically, an incision (or slit) 1061 is made into the tabbed blank leaving a portion 1062 of the donor material beneath the incision intact (FIG. 5G). The thickness of the intact portion 1062 is equal to the desired thickness of the tabs 106 (FIGS. 5I–5K). The trephine 6 is left in place such that the tab stroma is now confined on a fifth of the six possible planes by the blade of the trephine as illustrated in FIG. 4.

Using a scalpel 9, positioned by the lateral slots 520 of the guide 5 forming the upper scalpel guide and the lower scalpel guide 401 of the die 4, the stroma of the tab 106 is cut away from the Bowman's membrane 1062 of the donor blank 1021. In this manner, the scalpel 9 is used to trim the undesired portion of the donor blank 1021 using the scalpel guide and the trephine 6 blade as support for the donor material as illustrated in FIG. 4. The resultant donor material now has the desired shape as illustrated in FIGS. 5I–5K including thin tabbed portions 106.

Figure 1:
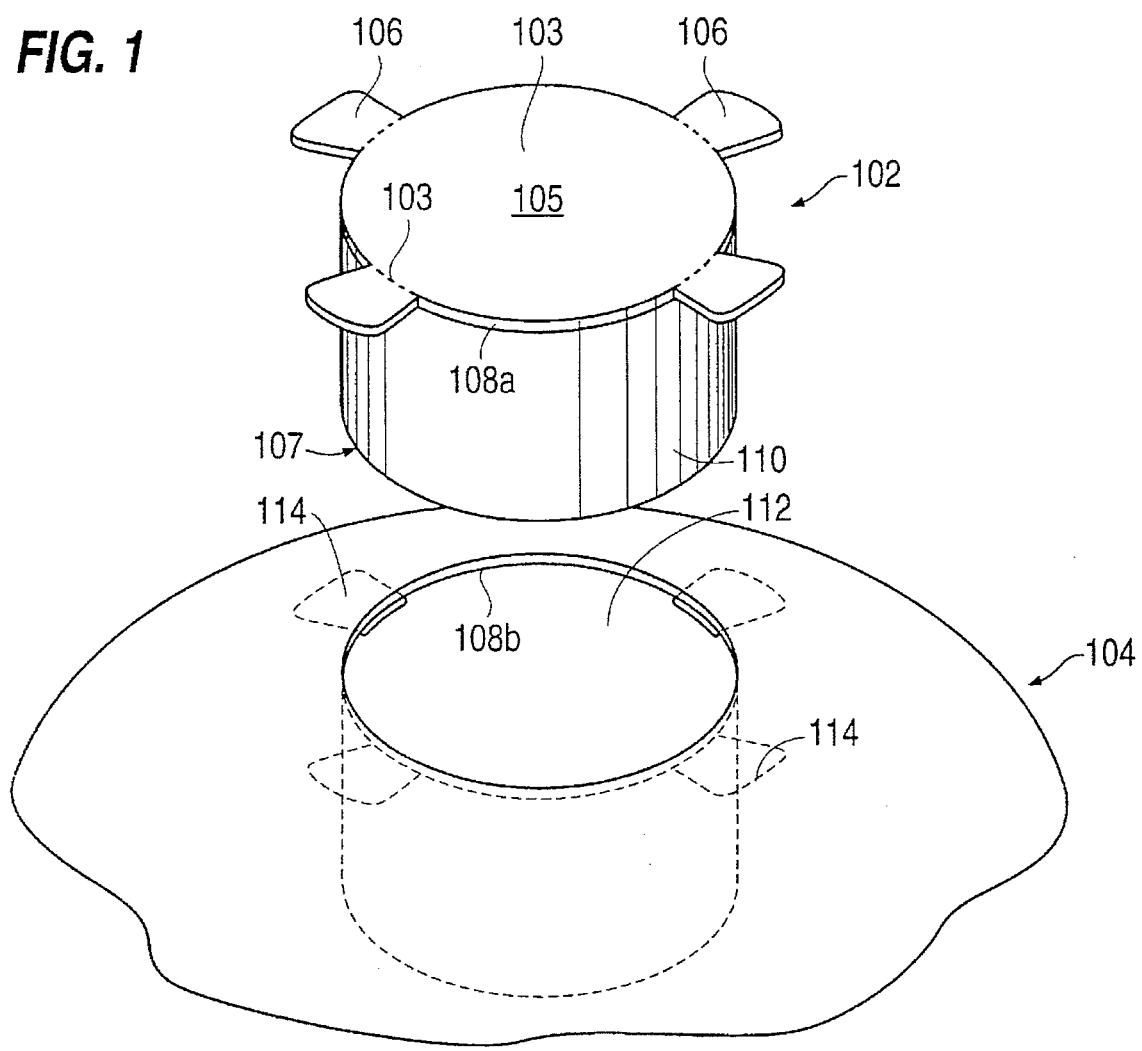
FIG. 1 illustrates the sutureless corneal transplant to which the instant invention is directed.
Figure 2:
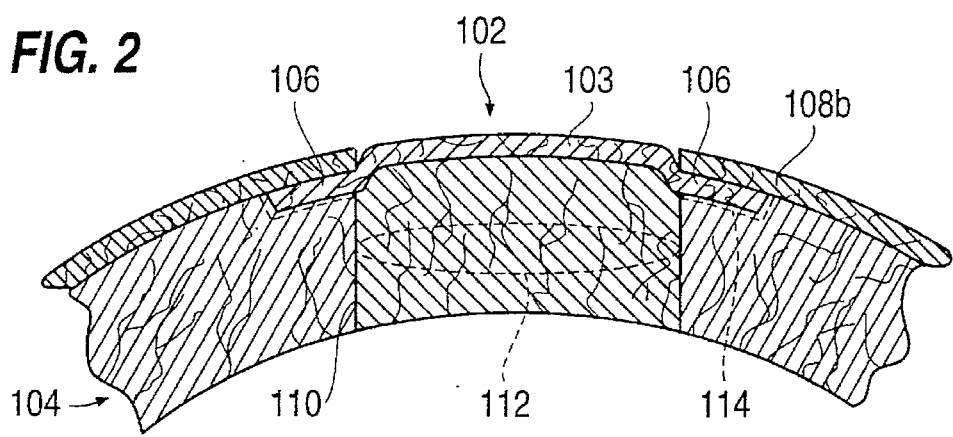
FIG. 2 illustrates a repaired eye using the sutureless corneal transplantation of FIG. 1.

Once the donor material is trimmed using the scalpel 9 to produce the donor material as illustrated in FIGS. 5I–5K, the scalpel 9, the round trephine 6 and the guide 5 are removed. The donor material 102 may then be removed from the die 4 and has the shape illustrated in FIGS. 1 and 5I–5J. The donor material is placed into the recipient's eye as illustrated in FIG. 2.

In this manner, the tool of the first embodiment of the instant invention is used to prepare donor material for implantation into the recipient eye. A tool for preparation of donor material according to a second embodiment of the instant invention will now be described in connection with FIGS. 6A–6D and 7A–7C.

Figure 3C:
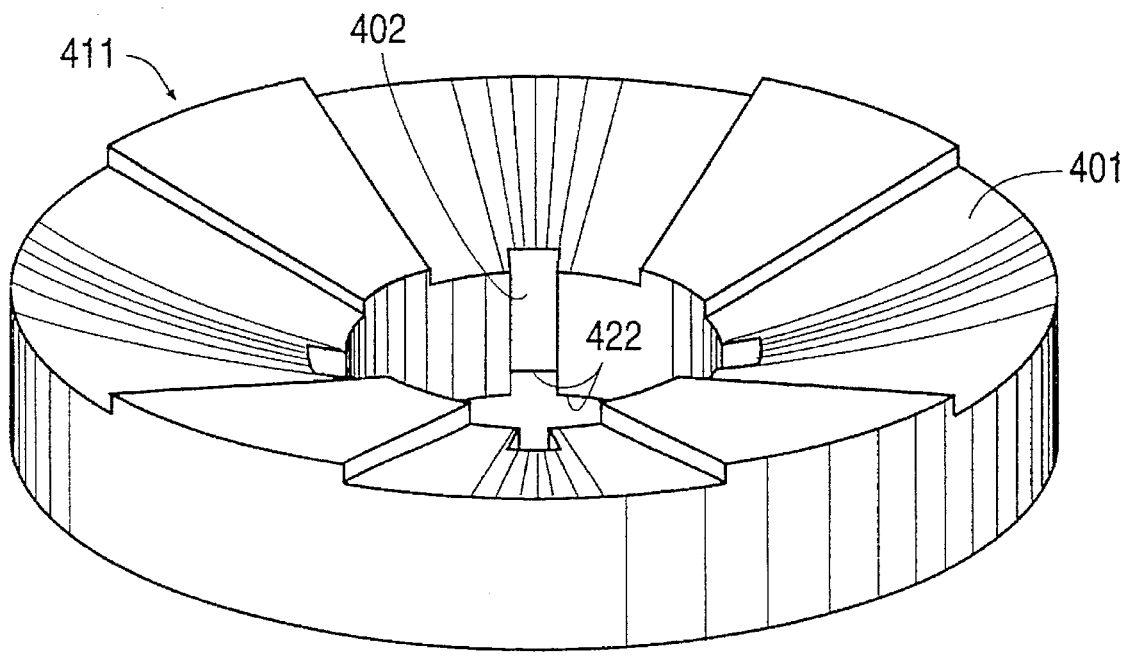
Figure 3D:
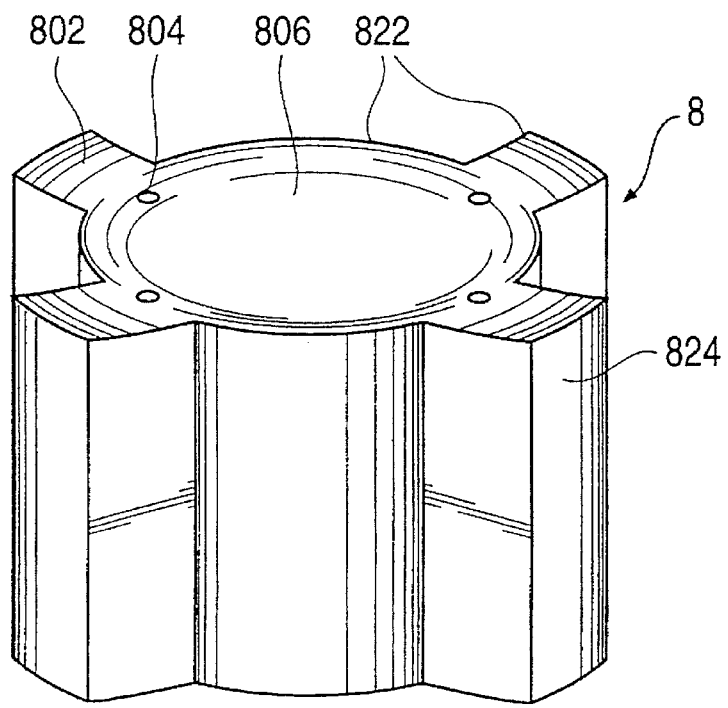

The second embodiment differs from the first embodiment in the manner in which the tabbed portions of the donor material are thinned. In accordance with the second embodiment, a two-stage process is employed. The first stage of the process utilizes a tool substantially similar to the tool depicted in FIGS. 3A and 3B. In the first stage, the donor material is cut into the desired shape including the tabs to produce a donor blank having cylindrical slits 1061 cut where the tabbed portions 1060 join the center portion 1050 as illustrated in FIG. 5G. In other words, a tool similar to that depicted in FIGS. 3A and 3B is used to prepare the donor material in the desired shape and to cut down into the central round portion of the donor material to the desired thickness. The donor material having the tabbed shape and the slits cut into the stroma shown in FIG. 5G will be referred to hereinafter as a cut donor blank 701. Since a thinning scalpel is not used in the second embodiment, it is readily understood that the tool illustrated in FIGS. 3A and 3B would not need to include the upper and lower scalpel guides 520 and 401 (FIGS. 3C and 4). Otherwise, the tool is used substantially as shown therein to prepare the cut donor blank 701 illustrated in FIG. 5G.

Figure 6A:
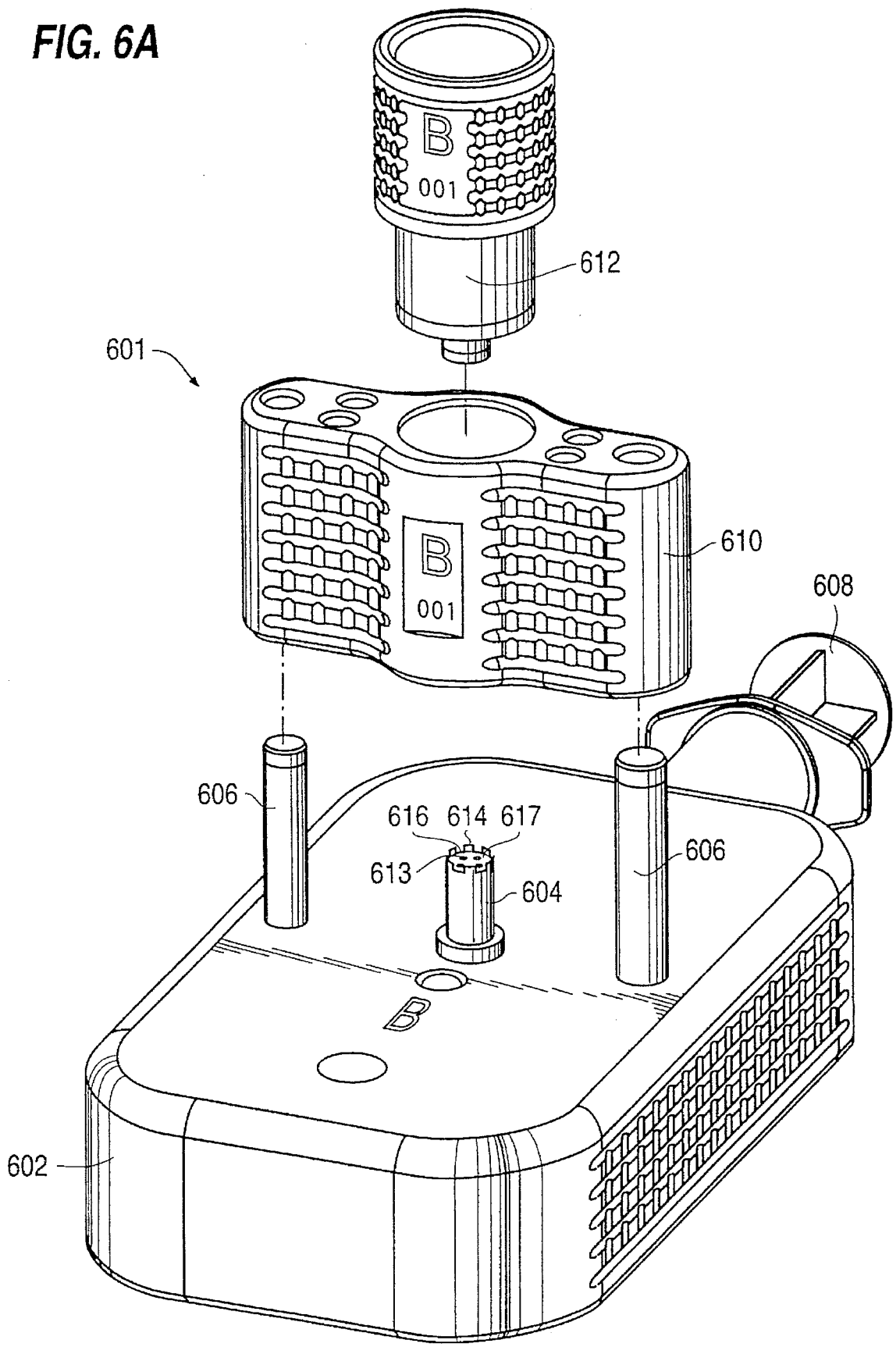
FIGS. 6A–6D illustrate a tool for preparing donor material according to a second embodiment of the instant invention.
Figure 6B:
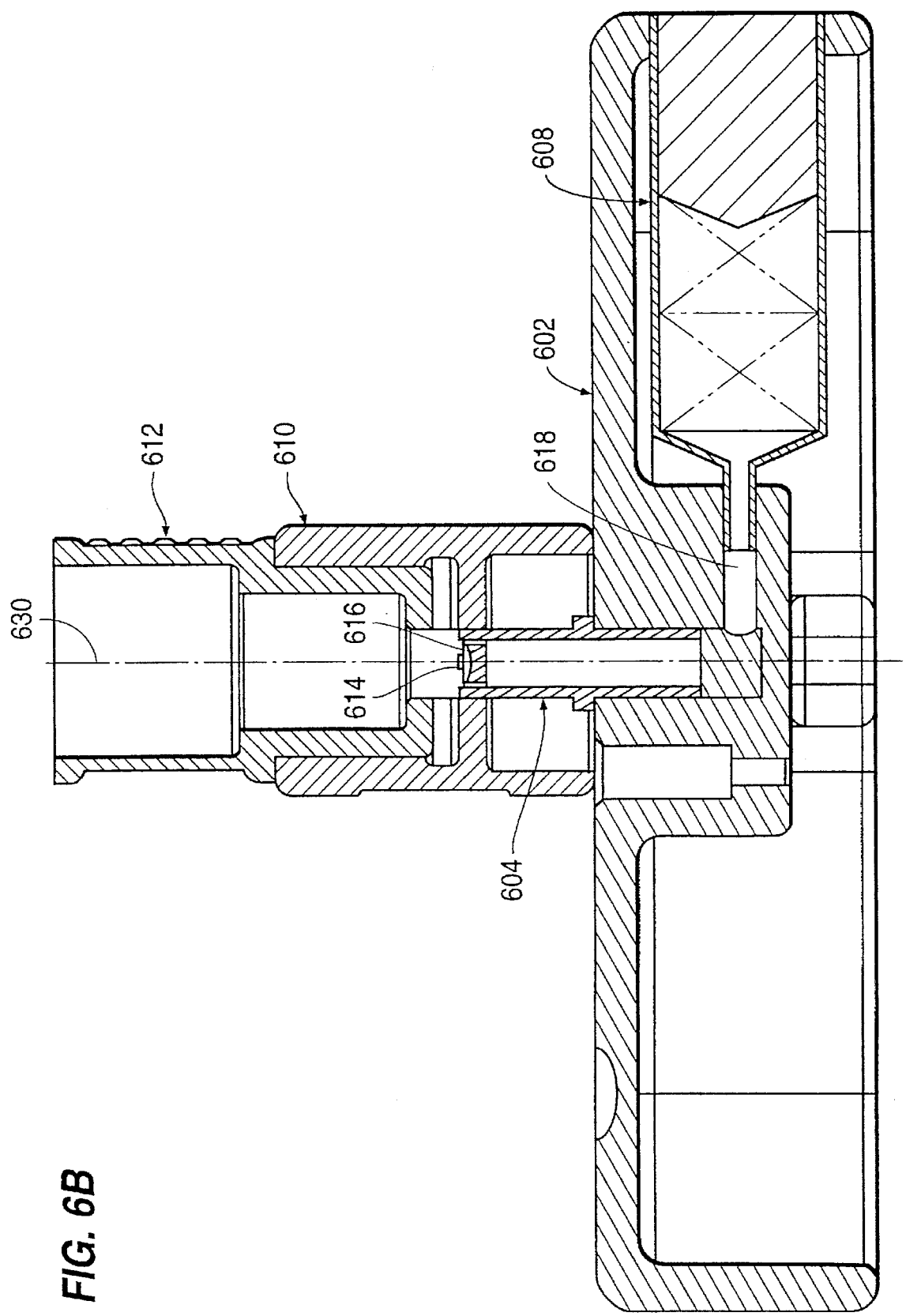
Figure 6C:
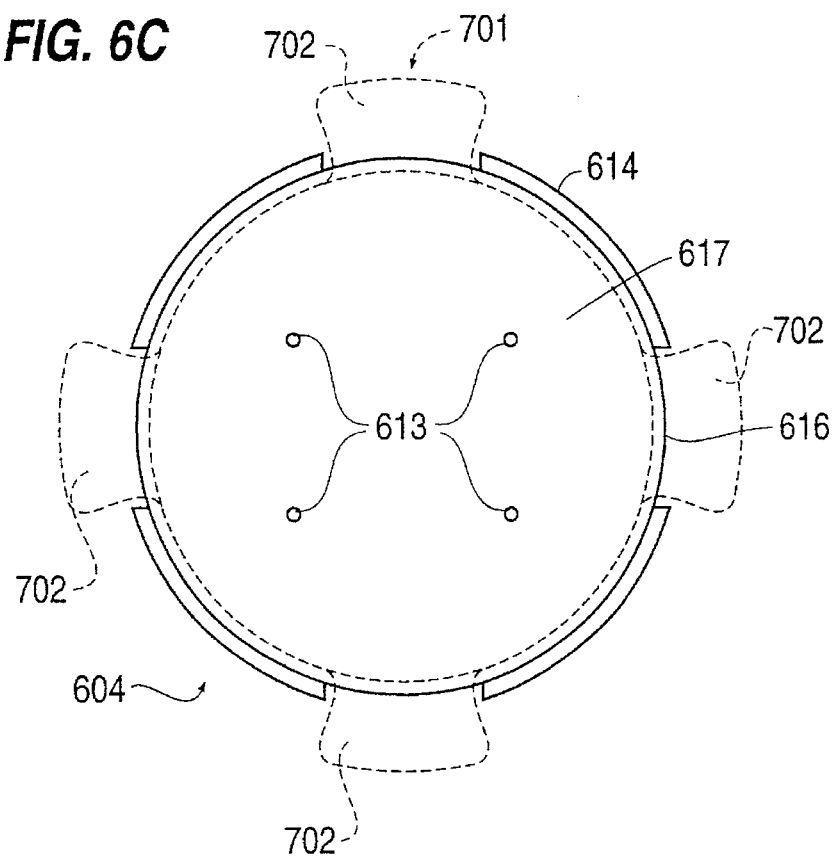
Figure 6D:
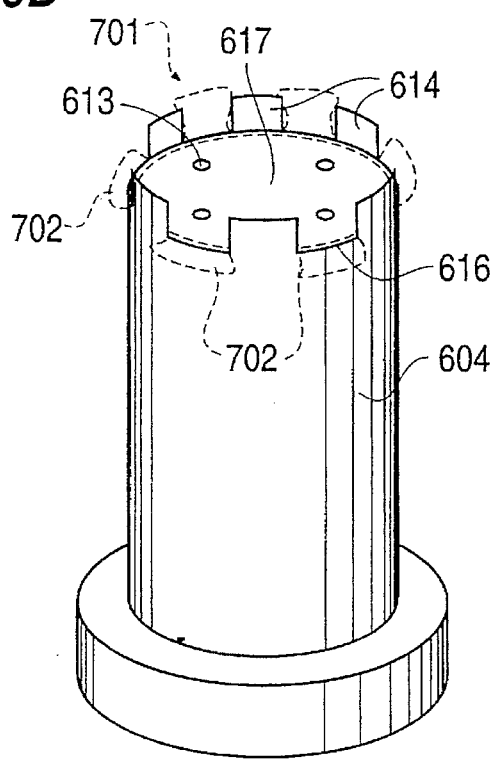
Figure 7A:
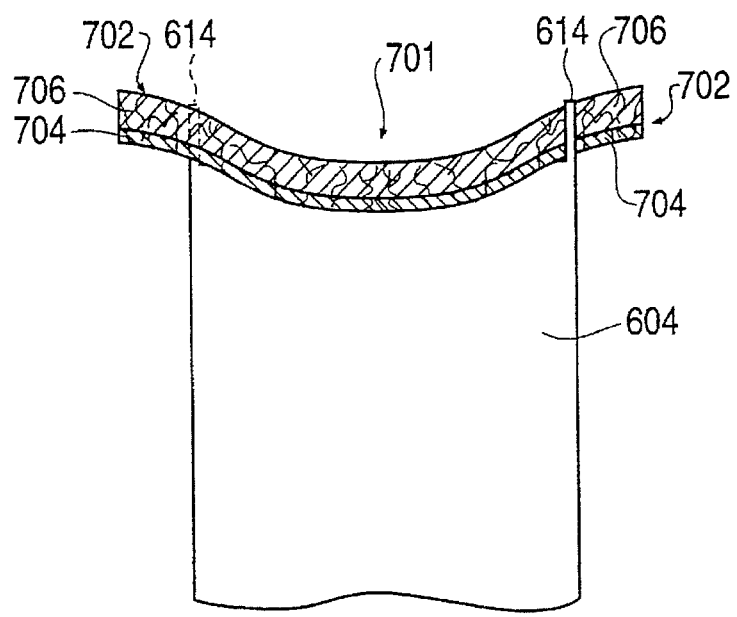
FIGS. 7A–7D illustrate the operation of the tool depicted in FIG. 6A–6D.

FIGS. 6A and 6B illustrate a tool for carrying out the second stage of the second embodiment of the instant invention. The second stage is for removing the stroma material 706 from the tabbed portions 702 of the cut donor blank 701 (FIG. 7A). In FIGS. 6A and 6B there is illustrated a base 602, a castellated nest 604, guide pins 606, a syringe 608, a tab-bender 610, and a second round trephine 612. The operation of the tool is described below in connection with FIGS. 6A–6D and FIGS. 7A–7D.

The cut donor blank 701 is placed on the castellated nest 604 (FIG. 7A). Around the periphery of the top surface 617 of the castellated nest 604 are a plurality of pillars 614 (castellations) with spaces 616 therebetween (FIGS. 6C and 6D. The shape of the pillars 614 and spaces 616 correspond to that of the cut donor blank 701 which rests on the top surface 617 of the castellated nest 604 with the tabbed portions extending outward radially through the spaces 616 (FIGS. 6D and 7A). A top and side view of the castellated nest 604 is illustrated in FIGS. 6C and 6D, respectively. As can be seen in FIGS. 6C and 6D, the tabbed portions 702 of the cut donor blank 701 (dotted lines) extend through the spaces 616 between the pillars 614 of the castellated nest 604. The cut donor blank 701 is held in place by suction induced by the syringe 608. As illustrated in FIG. 6B, the syringe 608 generates a suction through an air canal 618 and draws air out of holes 613 (FIGS. 6C and 6D) on the top surface 617 of the castellated nest 604. This suction is used to hold the cut donor blank in place during the operation of the tab thinning tool 601.

Figure 7B:
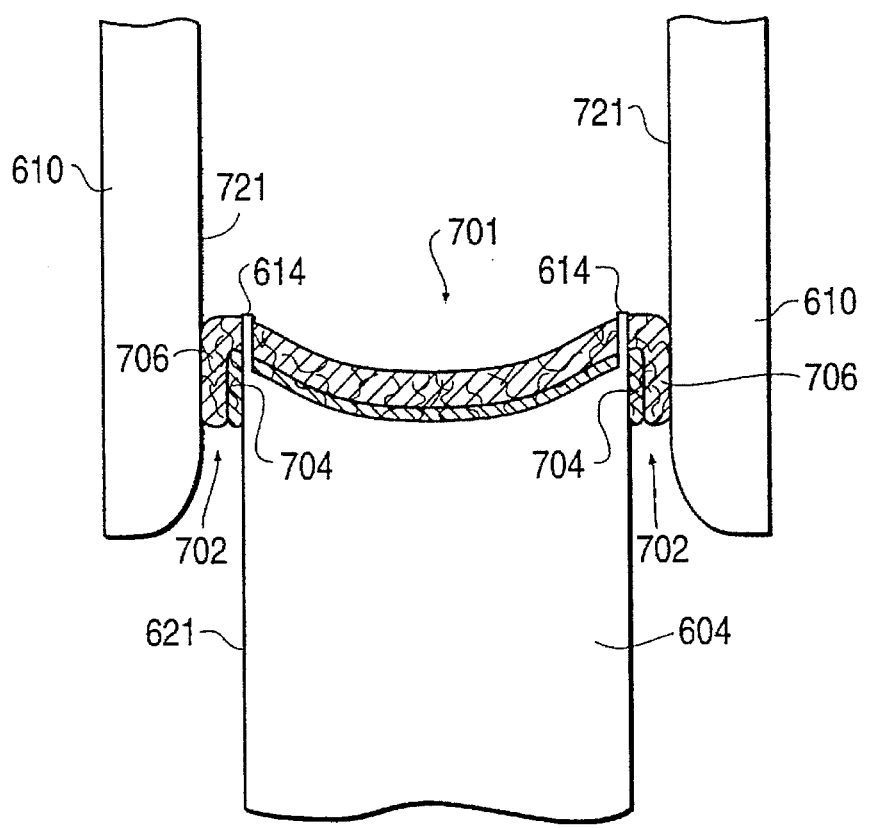

While the cut donor blank 701 is secured in place by the syringe 608 (FIG. 7A), the tab bender 610, guided by the guide pins 606, is lowered to the base 602 (FIGS. 6A and 6B). As a result, the tabs are bent at an angle of approximately 90 degrees to the configuration as illustrated in FIG. 7B. It is noted that in this state, the tabbed portions 702 are held in place by the stroma 706 of the tabs 702 as the stroma 706 contacts the inside wall 721 of the tab bender 610. This operation forces the Bowman's membrane 704 of the tabbed portion 702 into contact with the outer wall 621 of the castellated nest 604.

Figure 7C:
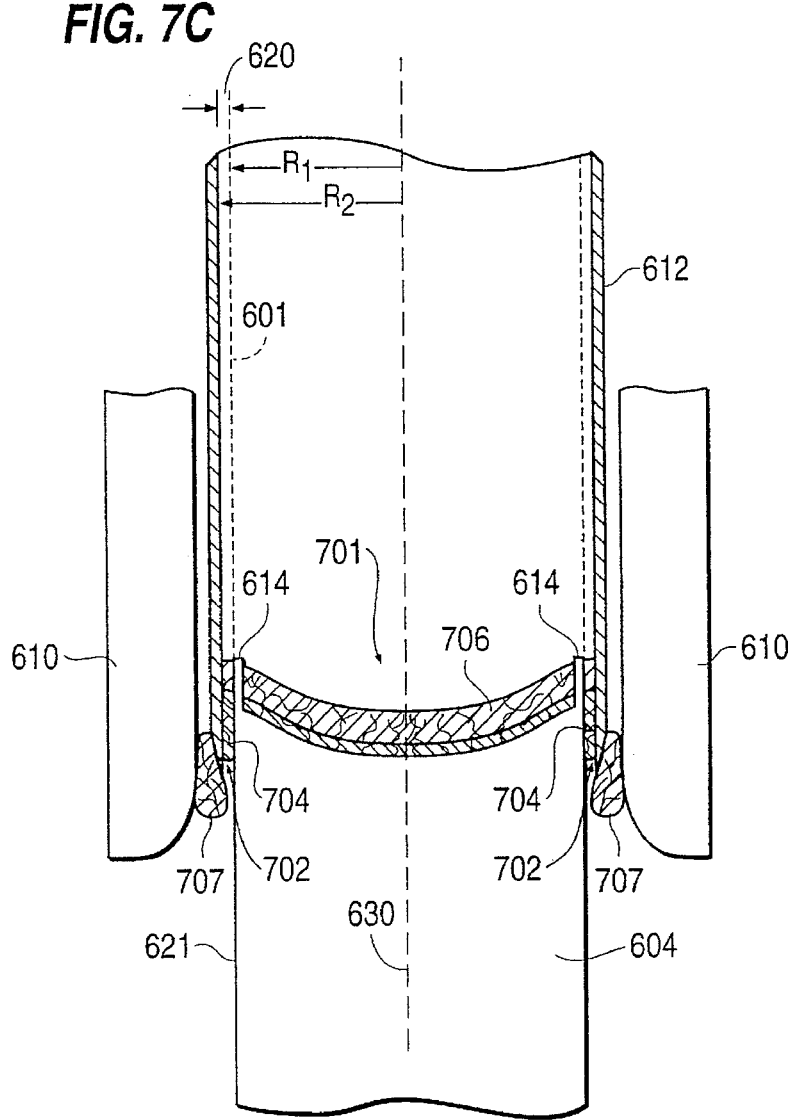

Once the tab bender 610 has secured the tab portions 702 in place, a round trephine 612 is inserted into the hollow portion of the tab bender as illustrated in FIG. 7C in the direction along a central axis 630 of the center of the cut donor blank 701. The round trephine 612 is brought down in an oscillating motion to cut a portion 707 of the stroma 706 from the tabs 702 leaving only the Bowman's membrane 704 on the tabbed portions 702. As can be understood from the diagram in FIG. 7C, the thickness of the remaining part of the tabbed portions 704 is determined as a function of the radius $R_1$ of the outer wall 621 of the castellated nest 604 (which corresponds substantially to the radius of the first round trephine 601 used to prepare the cut donor blank 701) and the radius R2 of the second round trephine 612 used to trim (or thin) the tabbed members. As can be seen, the thickness of the remaining tabbed material 702 will be essentially the difference 620 between R1 and R2. The concentricity between the second round trephine 612 and the outer wall 621 of the castellated nest 604 is critical. The eccentricity should be held to a maximum of 0.0002".

Figure 7D:
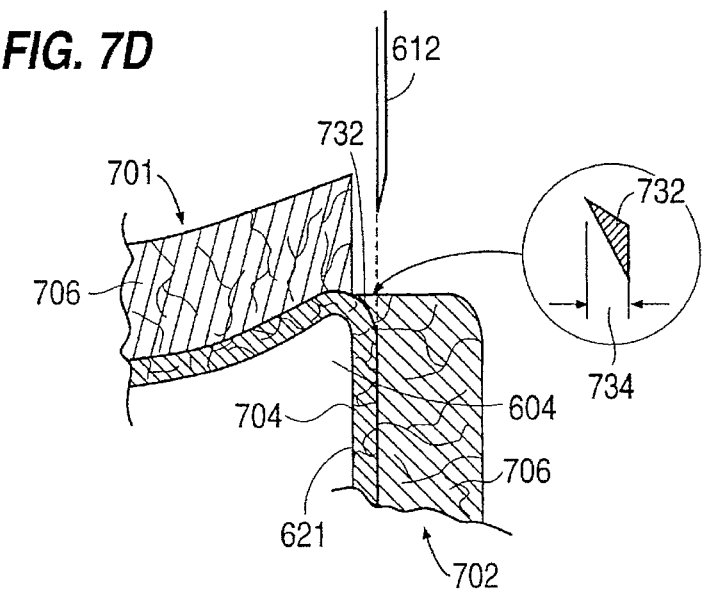

FIG. 7D illustrates an expanded view of the cut donor blank 701 as it extends over the castellated nest 604 and is held against the outer wall 621 of the castellated nest 604 by the tab bender 610 (not shown). While a small portion 732 of the stroma will remain on the tab 702 after the bulk of the stroma 707 on the tab 702 is cut away by the second round trephine 612, it does not interfere with the imbrication of the donor material 102 into the recipient eye 104 (FIG. 1). The thickness of the portion 732 not cut away by the trephine 612 is approximately 0.0005" at its thickest portion.

Once the stroma is cut from the tabbed material, the round trephine 612 is removed from the device. If necessary, the syringe 608 can be used to hold the trimmed tabbed donor (blank) material in place while the round trephine 612, as well as the tab bender 610, are removed.

In accordance with the second embodiment, the tabbed portions of the donor material can be precisely thinned to a desired thickness as a simple function of the trephine radii (and the castellated nest) and does not require an exceptional skill on the part of the surgeon operating the tool.

The instant invention is not limited to the apparatus and methods illustrated in the above-described embodiments. Modifications, without departing from the scope of the inventive features therein, will be apparent to one of ordinary skill in the art having reviewed the above description. Accordingly, the instant invention is not limited to the embodiments described above and is only limited by the appended claims.

What is claimed is:

1. A tool for thinning at least one tabbed portion of donor material having a predetermined shape, the tabbed portion extending outward radially from a center portion of the donor material, said tool comprising:

a nest having a top surface and outer wall extending downward from the top surface, the nest being adapted to hold the donor material, the nest having a shape such that the tabbed portion of the donor material extends beyond the periphery of the top surface of the nest defined by the outer wall;

a tab bender adapted to be inserted over the nest, a distance between an inside wall of the tab bender and the outer wall of the nest being approximately equal to a thickness of the tabbed portion, wherein the inside wall of the tab bender bends the tabbed portion and presses the tabbed portion against a part of the outer wall of the nest when the tab bender is inserted over the nest; and a cutting tool adapted to be inserted between the inside wall of the tab bender and the outer wall of the nest, the cutting tool dimensioned to cut off a part of the tabbed portion adjacent to the inside wall of the tab bender;

wherein a first radial distance to the outer wall of the nest is less than a second radial distance to an inner wall of the cutting tool such that the difference between the first radial distance and the second radial distance is substantially equal to a thickness of a Bowman's membrane of the donor material.

2. An apparatus as recited in claim 1, further comprising a suction device operable to hold the donor material in place when the tab bender is inserted over the nest.

* * * * *